United States Patent
Weiss et al.

(10) Patent No.: US 9,593,981 B2
(45) Date of Patent: Mar. 14, 2017

(54) NANOSCALE POROUS GOLD FILM SERS TEMPLATE

(75) Inventors: Sharon M. Weiss, Franklin, TN (US); Yang Jiao, Nashville, TN (US); Judson D. Ryckman, Nashville, TN (US); Peter N. Ciesielski, Lakewood, CO (US); G. Kane Jennings, Franklin, TN (US)

(73) Assignee: Vanderbilt University, Nashville, TN (US)

(*) Notice: Subject to any disclaimer, the term of this patent is extended or adjusted under 35 U.S.C. 154(b) by 0 days.

(21) Appl. No.: 13/825,152

(22) PCT Filed: Sep. 20, 2011

(86) PCT No.: PCT/US2011/001627
§ 371 (c)(1),
(2), (4) Date: Mar. 20, 2013

(87) PCT Pub. No.: WO2012/039764
PCT Pub. Date: Mar. 29, 2012

(65) Prior Publication Data
US 2013/0182249 A1     Jul. 18, 2013

Related U.S. Application Data

(60) Provisional application No. 61/403,707, filed on Sep. 20, 2010.

(51) Int. Cl.
*G01J 3/02*     (2006.01)
*B82Y 30/00*     (2011.01)
(Continued)

(52) U.S. Cl.
CPC ............ *G01J 3/0267* (2013.01); *B21D 22/00* (2013.01); *B82Y 30/00* (2013.01); *B82Y 40/00* (2013.01); *G01J 3/44* (2013.01); *G01N 21/658* (2013.01)

(58) Field of Classification Search
CPC .......... G01J 3/44; G01J 3/4412; G01J 3/0267; G01N 21/65; G01N 21/658; B21D 22/00
(Continued)

(56) References Cited

U.S. PATENT DOCUMENTS 5,017,007 A *   5/1991   Milne et al. ................. 356/301
5,468,606 A     11/1995   Bogart et al.
(Continued)

FOREIGN PATENT DOCUMENTS

WO     WO 2009062757 A1 *   5/2009

OTHER PUBLICATIONS

"Gold Films with imprinted cavities" Dreier et al., J. Phys. Chem. Lett., published on web Nov. 25, 2009, pp. 260-264.*
(Continued)

*Primary Examiner* — Tarifur Chowdhury
*Assistant Examiner* — Mohamed K Amara
(74) *Attorney, Agent, or Firm* — Michael Best & Friedrich LLP

(57) ABSTRACT

Provided are patterned nanoporous gold ("P-NPG") films that may act as at least one of an effective and stable surface-enhanced Raman scattering ("SERS") substrate. Methods of fabricating the P-NPG films using a low-cost stamping technique are also provided. The P-NPG films may provide uniform SERS signal intensity and SERS signal intensity enhancement by a factor of at least about $1\times10^7$ relative to the SERS signal intensity from a non-enhancing surface.

16 Claims, 8 Drawing Sheets

(51) Int. Cl.
    *B82Y 40/00*    (2011.01)
    *G01N 21/65*    (2006.01)
    *B21D 22/00*    (2006.01)
    *G01J 3/44*     (2006.01)

(58) Field of Classification Search
    USPC ............... 356/301, 51; 117/84, 88, 95, 106; 205/112; 427/164
    See application file for complete search history.

(56) References Cited

U.S. PATENT DOCUMENTS

| | | | |
|---|---|---|---|
| 6,165,911 A * | 12/2000 | Calveley | B29C 43/003 257/E21.237 |
| 6,248,539 B1 | 6/2001 | Ghadiri et al. | |
| 7,027,163 B2 | 4/2006 | Angeley | |
| 7,195,733 B2 | 3/2007 | Rogers et al. | |
| 7,226,733 B2 | 6/2007 | Chan et al. | |
| 7,271,896 B2 | 9/2007 | Chan et al. | |
| 7,410,763 B2 | 8/2008 | Su et al. | |
| 7,450,227 B2 * | 11/2008 | Dwight et al. | 356/301 |
| 7,517,656 B2 | 4/2009 | Martin et al. | |
| 7,582,486 B2 | 9/2009 | Gollier et al. | |
| 7,618,250 B2 | 11/2009 | Van Santen et al. | |
| 7,692,771 B2 | 4/2010 | Kolesnychenko et al. | |
| 7,843,562 B2 | 11/2010 | Chan et al. | |
| 8,349,617 B2 | 1/2013 | Weiss et al. | |
| 8,932,475 B2 * | 1/2015 | Zu | 216/11 |
| 2005/0186515 A1 * | 8/2005 | Watkins | B82Y 10/00 430/322 |
| 2005/0191419 A1 * | 9/2005 | Helt | B82Y 10/00 427/256 |
| 2005/0246021 A1 * | 11/2005 | Ringeisen | A61B 17/0642 623/17.11 |
| 2006/0063178 A1 | 3/2006 | Rauh-Adelmann et al. | |
| 2006/0152147 A1 | 7/2006 | Lee et al. | |
| 2007/0115469 A1 * | 5/2007 | Ebstein | 356/301 |
| 2008/0157235 A1 | 7/2008 | Rogers et al. | |
| 2008/0208351 A1 | 8/2008 | Besenbacher et al. | |
| 2009/0093879 A1 | 4/2009 | Wawro et al. | |
| 2009/0140458 A1 | 6/2009 | Xu et al. | |
| 2009/0269587 A1 * | 10/2009 | Dressick et al. | 428/411.1 |
| 2009/0273119 A1 | 11/2009 | Imai | |
| 2009/0279085 A1 | 11/2009 | Ebstein | |
| 2010/0001848 A1 * | 1/2010 | McAllister | H04L 9/00 340/10.51 |
| 2010/0084376 A1 | 4/2010 | Khusnatdinov et al. | |
| 2010/0106233 A1 | 4/2010 | Grant et al. | |
| 2011/0056398 A1 | 3/2011 | Weiss | |
| 2014/0043607 A1 * | 2/2014 | Wang et al. | 356/301 |

OTHER PUBLICATIONS

"Imprinting well-controlled nanopore in organosilicate dielectric films..", to Lee et al., Adv. Mater. 2005.*
Patterning colloidal monolayer films using microcontact particle stripping to Andersson et al., Nanotechnology 18 (2007) 205303.*
"Platinum-plated nanoporous gold: An efficient, low Pt loading electro-catalyst for PEM fuel cells" to Zeis, Journal of Power Sources 165, (2007) 65-72.*
Direct Imprinting of Porous Substrates: A Rapid and Low-Cost. Approach for Patterning Porous Nanomaterials, to Ryckman et al.; Pubs. acs.org/Nanolett, pp. 1857-1862 (published on Sep. 17, 2010).*
"Direct Imprinting of Porous Substrates: A Rapid and Low-Cost. Approach for Patterning Porous Nanomaterials", to Ryckman et al.; Pubs. acs.org/Nanolett, pp. 1857-1862 (published on Sep. 17, 2010).*
United States Patent Office Action for U.S. Appl. No. 12/790,905 dated Mar. 23, 2016 (5 pages).*
United States Patent Office Action for U.S. Appl. No. 14/103,811 dated Jun. 6, 2015 (6 pages).*
Kumar et al.. "Features of gold having micrometer to centimeter dimensions can be formed through a combination of stamping with an elastomeric stamp and an alkanethiol "ink" followed by chemical etching"; App. Phys. Lett 63 (14), 1993.*
Gates et al. "New Approaches to Nanofabrication: Molding, Printing, and Other Techniques", Chem. Rev. 2005, 105, 1171-1196.*
Helt et al. "A Benchtop Method for the Fabrication and Patterning of Nanoscale Structures on Polymers", J Am. Chem. Soc. 2004, 126, 628-634.*
United States Patent Office Action for U.S. Appl. No. 12/790,908 dated Jul. 8, 2014 (6 pages).
U.S. Appl. No. 61/182,451, filed May 29, 2009.
U.S. Appl. No. 61/735,871, filed Dec. 11, 2012.
U.S. Appl. No. 61/750,638, filed Jan. 9, 2013.
U.S. Appl. No. 61/849,111, filed Jan. 18, 2013.
U.S. Appl. No. 61/754,563, filed Jan. 19, 2013.
U.S. Appl. No. 14/103,811, filed Dec. 11, 2013.
Alexander, T.A. et al., "Characterization of a commercialized SERS-active substrate and its application to the identification of intact *Bacillus endospores*," Appl. Optics (2007) 46(18):3878-3890.
Bok, H. M. et al., "Multiple surface plasmon modes for a colloidal solution of nanoporous gold nanorods and their comparison to smooth gold nanorods," Nano Lett. 8, 2265-2270 (2008).
Bosman, M. et al., "Light Splitting in Nanoporous Gold and Silver," ACS Nano 6, 319-326 (2012).
Chu, Y. et al., "Double-resonance plasmon substrates for surface-enhanced raman scattering with enhancement at excitation and stokes frequencies," ACS Nano (2010) 4:2804-2810.
Ciesielski , P.N. et al., "Functionalized nanoporous gold leaf electrode films for the immobilization of photosystem I," ACS Nano (2008) 2:2465-2472.
Cunin, F. et al., "Biomolecular screening with encoded porous-silicon photonic crystals," Nat. Mater. 1, 39-41 (2002).
Del Campo, A. et al., "Fabrication approaches for generating complex micro- and nanopatterns on polymeric surfaces," Chem Rev 108, 911-945 (2008).
Ding, Y. et al., "Nanoporous golf leaf: 'ancient technology'/advanced material," Adv. Mater. (2004) 16(21):1897-1900.
Freese, W. et al., "Design of binary subwavelength multiphase level computer generated holograms," Opt. Lett. 35, 676-678 (2010).
Fu, Y. Q. et al., "Diffractive optical elements with continuous relief fabricated by focused ion beam for monomode fiber coupling," Opt. Express 7, 141-147 (2000).
Gates, B. D. et al., "New approaches to nanofabrication: Molding, printing, and other techniques," Chem Rev 105, 1171-1196 (2005).
Geissler, M. et al., "Patterning. Principles and Some New Developments," Adv Mater 16, 1249-1269 (2004).
Gharghi, M. et al., "A Carpet Cloak for Visible Light," Nano Lett. 11, 2825-2828 (2011).
Guo, C. et al., "Grayscale photomask fabricated by laser direct writing in metallic nano-films," Opt. Express 17, 19981-19987 (2009).
Guo, L. J., "Nanoimprint Lithography: Methods and Material Requirements," Adv Mater 19, 495-513 (2007).
Hrudey, P.C.P. et al., "Variable diffraction gratings using nanoporous electrodes and electrophoresis of dye ions," Nanoengineering: Fabrication, Properties, Optics and Devices IV, edited by E.A. Dobisz et al., Proc. of SPIE (2007) 6645:66450K1-12.
Hsu, K. H. et al., Electrochemical nanoimprinting with solid-state superionic stamps. Nano Lett. 7, 446-451 (2007).
Jane, A. et al., "Porous silicon biosensors on the advance," Trends in Biotechnology (2009) 27(4):230-239.
Jiao, Y. et al., "Patterned nanoporous gold as an effective SERS template. Nanotechnology 22," 5302 (2011).
Kasuga, T. et al., "Formation of titanium oxide nanotube," Langmuir (1998) 14:3160-3163.
Kneipp, K. et al., "Single molecule detection using surface-enhanced Raman scattering (SERS)" Phys. Rev. Lett. (1997) 78(9):1667-1670.
Kucheyev, S.O. et al., "Surface-enhanced Raman scattering on nanoporous Au," Appl. Phys. Lett. (2006) 89:053102-1-053102-3.

(56) References Cited

OTHER PUBLICATIONS

Lang, X. Y. et al., "Localized surface plasmon resonance of nanoporous gold," Appl. Phys. Lett. 98, 093701 (2011).
Lang, X.Y. et al., "Geometric effect on surface enhanced Raman scattering of nanoporoud gold: improving Raman scattering by tailoring ligament and nanopore ratios," Appl. Phys. Left. (2009) 94:213109-1-21310-3.
Larouche, S. et al., "Infrared metamaterial phase holograms," Nat. Mater. 11, 450-454 (2012).
Lawrie, J. L. et al., "Size-Dependent Infiltration and Optical Detection of Nucleic Acids in Nanoscale Pores," IEEE Trans. Nanotechnol. 9, 596-602 (2010).
Lee et al., "Fabrication of the Funnel-shaped Three-Dimensional Plasmonic Tip Arrays by Directional Photofluidization Lithography," (2010) ACS Nano 2, 2465-2472, 7175-7184.
Levy, U. et al., "Design, fabrication, and characterization of circular Dammann gratings based on grayscale lithography," Opt. Lett. 35, 880-882 (2010).
Li, A.P. et al., "Hexagonal pore arrays with a 50-420nm interpore distance formed by self-organization in anodic alumina," J. Appl. Phys. (1998) 84(11):6023-6026.
Liscidini, M. et al., "Gratings on porous silicon structures for sensing applications," in Conference on Lasers and Electro-Optics/International Quantum Electronics Conference, OSA Technical Digest (2008), paper CMG7, 2 pages.
Liscidini, M. et al., "Scattering-matrix analysis of periodically patterned multilayers with asymmetric unit cells and birefringement media," Physical Review B (2008) 77:035324, 11 pages.
Low, S. P., Williams, K. A., Canham, L. T. & Voelcker, N. H. Evaluation of mammalian cell adhesion on surface-modified porous silicon. Biomaterials 27, 4538-4546 (2006).
Moskovits, M. "Surface-enhanced spectroscopy," Rev. Mod. Phys. (1985) 57:783-826.
Park, J. H. et al., "Biodegradable luminescent porous silicon nanoparticles for in vivo applications," Nat. Mater. 8, 331-336 (2009).
PCT/US2011/001627 International Search Report dated Dec. 30, 2011 (3 pages).
Qian, L.H. et al., "Surface enhanced Raman scattering of nanoporous gold: smaller pore sizes stronger enhancements," Appl. Phys. Lett. (2007) 90:153120-1-153120-3.
Ruffato, G. et al., "Nanoporous gold plasmonic structures for sensing applications," Opt. Express 19, 13164-13170 (2011).
Ryckman, J. D. et al., "Direct Imprinting of Porous Substrates: A Rapid and Low-Cost Approach for Patterning Porous Nanomaterials," Nano Lett. 11, 1857-1862 (2011).
Ryckman, J.D. et al., "Low-cost optical microstructures fabricated by imprinting porous silicon," Advanced Fabrication Technologies for Micro-Nano Optics and Photonics III, edited by Winston V. Schoenfeld, Proc. of SPIE 7591 (2010) 759108-1 to 9.
Ryckman, J.D. et al., "Micron and submicron sized optical structures fabricated by imprinting porous silicon," Porous Semiconductors—Science and Technology Conference, Valencia, Spain, Mar. 2010, 2 pages.
Ryckman, J.D. et al., "Porous silicon structures for low-cost diffraction-based biosensing," Appl. Phys. Lett. (2010) 96:171103, 3 pages.
Sardana, N. et al., "Propagating surface plasmons on nanoporous gold," J Opt Soc Am B 29, 1778-1783 (2012).
Schleunitz, A. et al., "Selective profile transformation of electron-beam exposed multilevel resist structures based on a molecular weight dependent thermal reflow," J Vac Sci Technol B 29, F302 (2011).
Sipe, J.E. et al., "Enhancement of diffraction-based biosensing using porous structures and electromagnetic surface states," Proc. of SPIE 7553, 7553OM (Feb. 2010) 7 pages.
Sirbuly, D. J. et al., "Patterned microstructures of porous silicon by dry-removal soft lithography". Adv Mater 15, 149 (2003).
Smith, R.L. et al., "Porous silicon formation mechanisms," J. Appl. Phys. (1992) 71:R1-R22.
Sondergaard, T. et al., "Plasmonic black gold by adiabatic nanofocusing and absorption of light in ultra-sharp convex grooves," Nat. Commun. 3 (2012).
Sun, W. et al., "Nano- to microscale porous silicon as a cell interface for bone-tissue engineering," Adv Mater 19, 921 (2007).
Tascotti, E. et al., "Mesoporous silicon particles as a multistage delivery system for imaging and therapeutic applications," Nat. Nanotechnol. 3, 151-157 (2008).
United States Patent Office Action for U.S. Appl. No. 12/790,905 dated Apr. 3, 2012 (9 pages).
United States Patent Office Action for U.S. Appl. No. 12/790,908 dated Mar. 15, 2013 (9 pages).
United States Patent Office Action for U.S. Appl. No. 12/790,908 dated Sep. 10, 2012 (6 pages).
United States Patent Office Action for U.S. Appl. No. 12/790,908 dated Sep. 29, 2013 (8 pages).
United States Patent Office Action for U.S. Appl. No. 13/825,152 dated Apr. 7, 2014 (18 pages).
United States Patent Office Notice of Allowance for U.S. Appl. No. 12/790,905 dated Sep. 17, 2012 (8 pages).
Urquhart, K. S. et al., "Computer-Generated Holograms Fabricated by Direct Write of Positive Electron-Beam Resist," Opt. Lett. 18, 308-310 (1993).
Valentine, J. et al., "An optical cloak made of dielectrics," Nat. Mater. 8, 568-571 (2009).
Waits, C., A. et al., "Investigation of gray-scale technology for large area 3D silicon MEMS structures," Journal of Micromechanics and Microengineering 13, 170-177 (2003).
Wei, X. et al. "Guided mode biosensor based on grating coupled porous silicon waveguide," Opt. Express 19, 11330-11339 (2011).
Wei, X. et al., "Grating couplers on porous silicon planar waveguides for sensing applications," J. Appl. Phys. 104, 3113 (2008).
Wokaun, "Surface enhanced electromagnetic processes," Solid State Phys. (1984) 38:223-294.
Xia, Y. N. et al., "Complex optical surfaces formed by replica molding against elastomeric masters," Science 273, 347-349 (1996).
Yang, J. C. et al., "Enhanced Optical Transmission Mediated by Localized Plasmons in Anisotropic, Three-Dimensional Nanohole Arrays," Nano Lett. 10, 3173-3178 (2010).
Yu, F. et al., "Simultaneous excitation of propagating and localized surface plasmon resonance in nanoporous gold membranes," Anal Chem 78, 7346-7350 (2006).
Yu, W. X. et al., "Fabrication of refractive microlens in hybrid SiO2/TiO2 sol-gel glass by electron beam lithography," Opt. Express 11, 899-903 (2003).
Zaumseil, J. et al., "Three-dimensional and multilayer nanostructures formed by nanotransfer printing," Nano Lett. 3, 1223-1227 (2003).
Zentgraf, T. et al., "Plasmonic Luneburg and Eaton lenses. Nat. Nanotechnol," 6, 151-155 (2011).
Zentgraf, T. et al., "An Optical Janus Device for Integrated Photonics," Adv Mater 22, 2561-2564 (2010).
Zeon Corporation, Zeonrex Electornic Chemicals, ZEP520A Technical Report, "High Resolution Positive Electron Beam Resist," Version 1.01 (Apr. 2003) 12 pages).
Zheludev, N. I. et al., "From metamaterials to metadevices" Nat Mater 11, 917-924 (2012).
United States Patent Office Action for U.S. Appl. No. 12/790,908 dated May 7, 2015 (6 pages).
United States Patent Office Action for U.S. Appl. No. 14/103,811 dated Jun. 9, 2015 (9 pages).

* cited by examiner

NANOSCALE POROUS GOLD FILM SERS TEMPLATE

CROSS-REFERENCE TO RELATED APPLICATIONS

This application claims the benefit of priority to U.S. Provisional Patent Application No. 61/403,707, filed Sep. 20, 2010, the content of which is incorporated herein by reference in its entirety.

STATEMENT REGARDING FEDERALLY SPONSORED RESEARCH OR DEVELOPMENT

This invention was made with United States Government support under federal Grant No. W911NF-09-1-0101 awarded by the Army Research Office, federal Grant No. ECCS-0746296 awarded by the National Science Foundation, and federal Grant No. DMR-0907619 awarded by the National Science Foundation. The United States Government has certain rights in this invention.

BACKGROUND

Surface-enhanced Raman scattering ("SERS") is a surface sensitive technique that results in the enhancement of Raman scattering by molecules adsorbed on the surface. SERS provides a significant enhancement in scattering efficiency over normal Raman scattering primarily due to the intense electromagnetic field in close proximity to the metal surface where molecules are adsorbed.

SERS has been widely used for uniquely identifying molecules with high detection sensitivity in chemical and biological sensing.

SUMMARY

In one aspect, the disclosure may provide a SERS substrate comprising a nanoporous gold film having a pattern defined therein.

In another aspect, the disclosure may provide a SERS substrate. The substrate may comprise a nanoporous gold film, wherein SERS signal intensity is enhanced by a factor of at least about $1 \times 10^7$ relative to the SERS signal intensity from a non-enhancing surface.

In another aspect, the disclosure may provide a SERS substrate comprising patterned nanoporous gold film, wherein the patterned gold film enhances the SERS signal intensity by a factor of at least about $4 \times 10^2$ compared to the same nanoporous gold film without patterning.

In another aspect, the disclosure may provide a SERS substrate comprising a nanoporous gold film having ordered protrusions extending therefrom, the protrusions having a porosity of greater than about 10%.

In another aspect, the disclosure may provide a method of preparing a SERS substrate. The method may comprise patterning a first nanoporous gold film with a pattern.

In another aspect, the disclosure may provide a method of detecting an analyte. The method may comprise contacting a SERS substrate with a sample suspected of containing an analyte of interests, and obtaining a SERS spectrum of the sample, wherein the SERS substrate comprises a nanoporous gold film having a pattern defined therein.

Other aspects and embodiments are encompassed within the scope of the disclosure and will become apparent in light of the following description and accompanying Drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION

Figure 1:
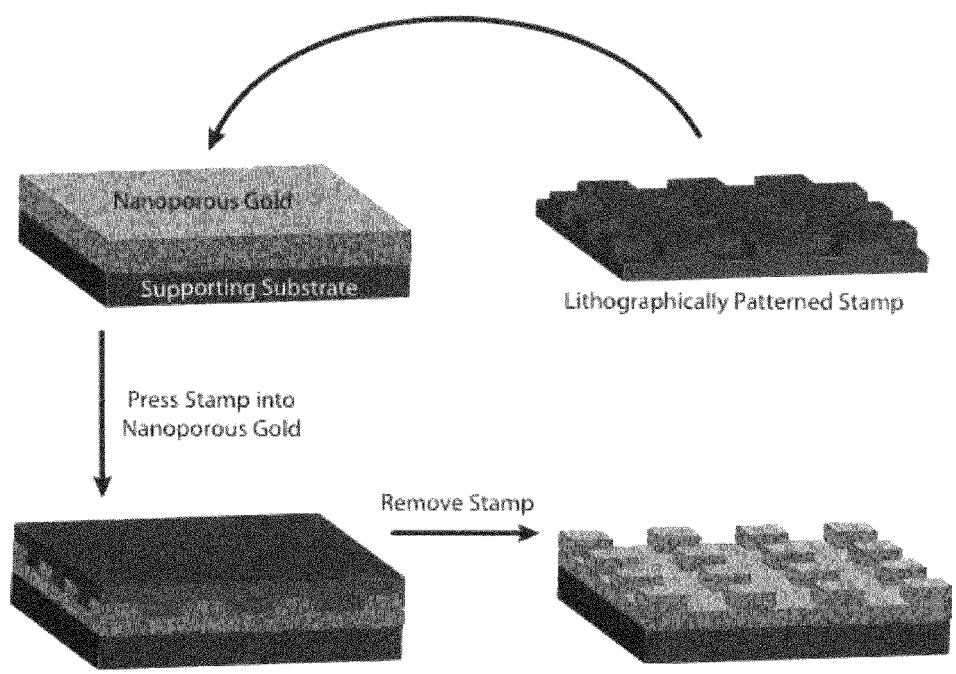
FIG. 1 shows a schematic fabrication process of a patterned nanoporous gold ("P-NPG") SERS substrate.

The present application provides a patterned nanoporous gold ("P-NPG") film that may act as at least one of an effective and stable surface-enhanced Raman scattering ("SERS") substrate, as well as a method of fabricating the P-NPG film using a low-cost stamping technique. The P-NPG films may provide at least one of uniform SERS signal intensity, SERS signal intensity enhancement by a factor of at least about $1 \times 10^7$, and a combination thereof. Stable SERS substrates with metallic nanoscaled surface morphologies have been demonstrated to enable high detection sensitivity and even single molecule detection. See, e.g., Moskovits, "Surface-enhanced Spectroscopy," *Rev. Mod. Phys.* 1985, 57, 783-826; Wokaun, "Surface Enhanced Electromagnetic Processes," *Solid State Phys.* 1984, 57, 223-294; and Kneipp et al., "Single Molecule Detection Using Surface-Enhanced Raman Scattering (SERS)," *Phys. Rev. Lett.* 1997, 78, 1667-1670. For example, nanoporous materials based substrates (Kucheyev et al., "Surface-enhanced Raman Scattering on Nanoporous Au," *Appl. Phys. Lett.* 2006, 89, 053102; Qian et al., "Surface Enhanced Raman Scattering of Nanoporous Gold: Smaller Pore Sizes Stronger Enhancements," *Appl. Phys. Lett.* 2007, 90, 153120; and Lang et al., "Geometric Effect on Surface Enhanced Raman Scattering of Nanoporous Gold: Improving Scattering by Tailoring Ligament and Nanopores Ratios," *Appl. Phys. Lett.* 2009, 94, 213109), electrochemically-roughened metal surfaces, and colloidal nanoparticles in solution or on a solid surface. Controllable SERS morphology by pressure has also been investigated using metal pellets of silver and copper.

Nanoporous gold ("NPG") has been demonstrated to be an attractive SERS template due to its chemical stability and unique sponge-like interacting nanoscaled structure. Modified NPG samples prepared via chemical methods have demonstrated further improved SERS signals due to the optimized pore size and gold ligament. However, these irregular SERS substrates commonly suffer from the lack of uniformity and reproducibility of the preparation process. For this reason, regular-structured particles, gratings, and holes arrays have attracted attention in the fabrication of more systematic and reproducible SERS substrates. Periodic silver particles array on silica, silver elliptical discs on silicon, and coupled quadrate holes and squares have been fabricated by electron beam ("e-beam") lithography, and dual-mode gold coated metallic holes array show the feasibility of both SERS and optical transmittance measurements. Although SERS substrates generated by e-beam lithography show uniform and stable SERS activity, their high cost and long single production cycle are major limitations to the mass production of cheap sensors.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc. are expressly enumerated in this specification. These are only examples of what is specifically intended.

Further, no admission is made that any reference, including any patent or patent document, cited in this specification constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinency of any of the documents cited herein.

This application provides at least one of a stable, effective, and easily-fabricated SERS-active substrate. The SERS-active substrate may comprise a patterned or stamped NPG substrate.

Nanoporous Gold

Nanoporous gold ("NPG") may be characterized by nanoscale voids and high specific surface area that gives rise to desirable optical, electrical, chemical, and mechanical properties. Nanoporous gold or NPG may include pure gold as well as gold alloys with additional chemical elements such as silver. The nanoporous gold or NPG may consist only of the above-mentioned elements or may consist essentially of such elements, or in other embodiments, may include additional elements. In some embodiments, the nanoporous gold may comprise about 45% or more, about 50% or more, about 55% or more, about 60% or more, about 65% or more, about 70% or more, 75% or more, about 80% or more, about 82% or more, about 84% or more, about 86% or more, about 88% or more, about 90% or more, about 91% or more, about 92% or more, about 93% or more, about 94% or more, about 95% or more, about 96% or more, about 97% or more, about 98% or more, or about 99% or more by weight gold. The pores of the material may be smaller than about 10 μm, typically smaller than about 1 μm, and more typically smaller than about 100 nm. The pores may be smaller than about 100 μm, smaller than about 50 μm, smaller than about 10 μm, smaller than about 5 μm, smaller than about 1 μm, smaller than about 500 nm, smaller than about 100 nm, smaller than about 50 nm, smaller than about 10 nm, or smaller than about 5 nm.

As used herein, porosity refers to the ratio of the volume of empty space over the volume of a unit structure, for a particular material. Because the porosity is a ratio, it is unitless. Porosity may be reported as a decimal number, a fraction, or a percentage. The porosity of the NPG used herein may be greater than about 10%, typically greater than about 25%, more typically greater than about 40%. The porosity may be greater than about 10%, about 15%, about 20%, about 25%, about 30%, about 35%, about 40%, about 45%, about 50%, about 55%, about 60%, about 65%, about 70%, about 75%, about 80%, about 85%, about 90%, or greater than about 95%. The porosity may be less than about 95%, about 90%, about 85%, about 80%, about 75%, about 70% about 65%, about 60%, about 55%, about 50%, about 45%, about 40%, about 35%, about 30%, about 25%, about 20%, about 15%, or less than about 10%. In some embodiments, the porosity of the NPG used herein may be about 20% to about 80%, about 30% to about 70%, or about 40% to about 60%.

Thickness of the NPG film may vary from about 50 nm to about 250 nm, particularly from about 65 nm to about 225 nm, and more particularly, from about 80 nm to about 200 nm. In some embodiments, the NPG film thickness may be greater than about 40 nm, greater than about 50 nm, greater than about 60 nm, greater than about 70 nm, greater than about 80 nm, greater than about 90 nm, greater than about 100 nm, greater than about 110 nm, greater than about 120 nm, greater than about 130 nm, greater than about 140 nm, greater than about 150 nm, greater than about 160 nm, greater than about 170 nm, greater than about 180 nm, greater than about 190 nm, greater than about 200 nm, greater than about 210 nm, greater than about 220 nm, greater than about 230 nm, or greater than about 240 nm. In some embodiments, the NPG film thickness may be less than about 250 nm, less than about 240 nm, less than about 230 nm, less than about 220 nm, less than about 210 nm, less than about 200 nm, less than about 190 nm, less than about 180 nm, less than about 170 nm, less than about 160 nm, less than about 150 nm, less than about 140 nm, less than about 130 nm, less than about 120 nm, less than about 100 nm, less than about 90 nm, less than about 80 nm, less than about 70 nm, or less than about 60 nm.

Porous materials offer a large internal surface area (about 100 $m^2/cm^3$) and highly tunable pore dimensions, making them particularly suitable for use in a variety of applications including photovoltaics, integrated optics, drug-delivery, and sensing of biological and chemical species. In some embodiments, the NPG is prepared from a gold alloy comprising, by weight, about 5% or more, about 10% or more, about 15% or more, about 20% or more, about 25% or more, about 30% or more, about 35% or more, about 40% or more, about 45% or more, about 50% or more, or about 51% or more of an alloying element such as silver. The gold alloy may comprise, by weight, about 45% or more, about 50% or more, about 55% or more, about 60% or more, about 65% or more, about 70% or more, about 75% or more, about 80% or more, about 85% or more, about 90% or more, or about 95% or more of gold. The gold alloy may be dealloyed in an electrolyte such as an acid (e.g., $HNO_3$ or HCl) of a concentration such as about 70% for about 15 minutes at about 22° C. to dissolve or selectively leach out the silver.

In some embodiments, the gold alloy is dealloyed in 70% HNO$_3$ at about 22° C. for about 2 hours or less, about 1 and half hours or less, about 1 hour or less, about 45 minutes or less, about 30 minutes or less, about 25 minutes or less, about 20 minutes or less, about 15 minutes or less, about 12.5 minutes or less, about 10 minutes or less, about 7.5 minutes or less, about 5 minutes or less, about 2.5 minutes or less, about 2 minutes or less, about 1.5 minutes or less, about 1.0 minutes or less, about 0.5 minutes or less to at least partially dissolve a percentage of the alloying element, e.g., silver. In further embodiments, the gold alloy can be dealloyed in an acid (e.g., HNO$_3$ or HCl) with a concentration of about 50%, 60%, 70%, 80% or 90%. The percentage of the dissolved element may be about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100% of the element content of the alloy. For example, by adjusting the dealloying time, temperature, concentration of the acid, or a combination thereof, the percentage of the dissolved element and degree of porosity can ultimately be controlled. Precise control over pore morphology can be obtained by varying anodization parameters such as current density, voltage, electrolyte composition, substrate doping, and process temperature. See, e.g., Li et al., "Hexagonal pore arrays with a 50-420 nm interpore distance formed by self-organization in anodic alumina," (1998) J. Appl. Phys. 84, 6023-6026; Ding et al., "Nanoporous gold leaf: 'ancient technology'/advanced material," (2004) Adv. Mater. 16, 1897-1900; Kasuga et al., "Formation of titanium oxide nanotube," (1989) Langmuir 14, 3160-3163; and Smith et al., "Porous silicon formation mechanisms," (1992) J. Appl. Phys. 71, R1-R22, each of which is incorporated by reference in its entirety.

Patterned Nanoporous Gold ("P-NPG") SERS Substrate Fabrication

The NPG may be patterned using photolithographic and etching methods known in the art. Additionally micromechanical components can be fabricated using compatible "micromachining" processes that selectively etch away parts of the NPG or add new structural layers to form mechanical and/or electromechanical components. Other basic construction techniques may include, but need not be limited to, depositing thin films of material on a substrate, applying a patterned mask on top of the films by some lithographic methods, and selectively etching the films. Deposition techniques of use can include chemical procedures such as chemical vapor deposition ("CVD"), electrodeposition, epitaxy and thermal oxidation and physical procedures like physical vapor deposition ("PVD") and casting. Structures produced with these techniques have smallest dimensions on the order of nanometers, however, structures produced with these techniques may be smaller than 100 µm, typically smaller than 10 µm, more typically smaller than 1 µm.

The P-NPG substrate may be fabricated via a direct imprinting technique such as is described in U.S. patent application Ser. No. 12/790,908, published as U.S. Publication No. 2011/0056398, the contents of which are hereby incorporated by reference in their entirety. Using this method, porous materials may be patterned on the micro- and nanometer scale to create structures of the invention using direct imprinting of porous substrates ("DIPS"). DIPS utilizes reusable stamps that may be directly applied to an underlying porous material to selectively, mechanically deform and/or crush, i.e., densify, particular regions of the porous material, creating a desired structure. The process can be performed in a matter of seconds, at room temperature or higher temperatures, and eliminates the requirement for intermediate masking materials and etching chemistries.

Stamps used in embodiments of the present application generally have a hardness greater than the hardness of the material being imprinted and can be pre-mastered i.e., they may have a patterned surface or surfaces. Pre-mastering of a stamp can be accomplished through conventional lithographic techniques, such as, for example, photolithography, reactive ion etching, electron beam lithography, wet etching, dry etching, focused ion-beam milling, laser machining, and combinations of these methods. In some embodiments, a pre-mastered stamp may be a reusable stamp. In some embodiments, a stamp material may comprise silicon. In some embodiments, the stamp may comprise a material with a material hardness of at least about 1 GPa, about 3 GPa, about 5 GPa, about 8 GPa, about 10 GPa, about 15 GPa, or at least about 20 GPa.

Applied pressures suitable for methods of the present application may commonly include pressures of about 50 N/mm$^2$ to about 500 N/mm$^2$, and more particularly, about 100 N/mm$^2$ to about 300 N/mm$^2$. In some embodiments, the applied pressure may be at least about 50, about 55, about 65, about 70, about 75, about 80, about 85, about 90, about 95, about 100, about 125, about 150, about 175, about 200, about 225, about 250, about 250, about 275, and at least about 300 N/mm$^2$.

Imprinting and overstamping may be accomplished by contacting the stamp with the NPG, exerting pressure as set forth above, and removing the stamp as set forth in FIG. 1. FIG. 1 shows a schematic for a fabrication process to prepare a P-NPG SERS substrate of the present application.

Methods of the present application can afford precise control over both lateral and vertical dimensions of patterning in a porous material while maintaining large area uniformity. In some embodiments of the present application, tunable imprint depths in the range of about 10 nm to about 1 µm, as well as lateral feature sizes below about 100 nm can be realized. The imprints may be less than about 100 µm, about 50 µm, about 20 µm, about 10 µm, about 100 nm, about 95 nm, about 90 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, about 5 nm, about 3 nm, and less than about 1 nm. The imprints may be greater than about 1 nm, about 5 nm, about 10 nm, about 15 nm, about 20 nm, about 25 nm, about 30 nm, about 35, about 40, about 45, about 50, about 55, about 65, about 70, about 75, about 80, about 85, about 90, about 95, and greater than about 100 nm. In some embodiments, the lateral feature size may be less than about 100 nm, about 95 nm, about 90 nm, about 80 nm, about 75 nm, about 70 nm, about 65 nm, about 60 nm, about 55 nm, about 50 nm, about 45 nm, about 40 nm, about 35 nm, about 30 nm, about 25 nm, about 20 nm, about 15 nm, about 10 nm, about 5 nm, about 3 nm, and less than about 1 nm. Imprinted structures may be characterized by scanning electron microscopy ("SEM"), atomic force microscopy ("AFM"), and optical diffraction experiments.

Methods of imprinting can commonly be carried out at temperatures ranging from about 15° C. up to about 1,200° C., particularly from about 20° C. up to about 200° C., or more particularly from about 21° C. to about 27° C.

In some embodiments, the imprint depth in the NPG can be less than about 1%, less than about 3%, less than about 5%, less than about 8%, less than about 10%, or less than about 15% of the height of the NPG that has not been imprinted. In some embodiments, the imprint depth can be greater than about 1%, greater than about 3%, greater than about 5%, greater than about 7%, greater than about 10%, greater than about 15%, and greater than about 20% of the height of the NPG that has not been imprinted.

In some embodiments, regions of the NPG may be compressed by less than about 20%, less than about 17%, less than about 15%, less than about 13%, less than about 10%, less than about 8%, less than about 5%, less than about 3%, less than about 2%, and less than about 1% up to about the porosity of the film relative to the NPG that has not been compressed. In some embodiments, regions of the NPG may be compressed by at least about 3%, at least about 5%, at least about 8%, at least about 10%, at least about 13%, at least about 15%, at least about 18%, at least about 20%, at least about 25%, at least about 30%, at least about 35%, or at least about 40% relative to the NPG that has not been compressed.

The porosity of the compressed i.e., imprinted, regions of the P-NPG may be greater than about 10%, typically greater than about 15%, more typically greater than about 20%. The porosity of the compressed regions of the P-NPG may be greater than about 10%, about 15%, about 20%, about 25%, about 30%, about 35%, about 40%, about 45%, about 50%, about 55%, about 60%, about 65%, about 70%, about 75%, about 80%, about 85%, about 90%, or greater than about 95%. The porosity of the compressed regions of the P-NPG may be less than about 95%, about 90%, about 85%, about 80%, about 75%, about 70% about 65%, about 60%, about 55%, about 50%, about 45%, about 40%, about 35%, about 30%, about 25%, about 20%, about 15%, or less than about 10%. In some embodiments, the porosity of the compressed regions of the P-NPG used herein may be about 10% to about 50%, about 15% to about 40%, or about 20% to about 30%.

In some embodiments, the stamp can be in contact with the NPG for about one second to about 2 minutes, particularly from about 1 second to about 5 seconds. In other embodiments, the stamp can be in contact for less than one second, and less than one half of one second.

In some embodiments, a single stamp may be used to contact the porous material at least a second time, where the stamp can be rotated, for example, greater than 90 degrees, about 90 degrees, or less than 90 degrees, between imprinting the porous material a first time and imprinting the porous material at least a second time. In some embodiments, more than one stamp may be used to contact the porous material, where the second stamp may include the same pattern as the first stamp or a different pattern than the first stamp. The second stamp may also be used to contact the porous material at least a second time, where the second stamp can be rotated, for example, greater than 90 degrees, about 90 degrees, or less than 90 degrees, between imprinting the porous material a first time with the second stamp and imprinting the porous material at least a second time with the second stamp.

In some embodiments, overstamping may produce a freestanding nanoparticle or microparticle. Generally, to produce a freestanding nanoparticle or microparticle, some region of the film can be imprinted to a significant fraction, i.e. approaching the original porosity of the film. For example, in some embodiments a first imprint fraction can be greater than 70%, followed by a second imprint region, imprinted often at least to about 10%. For example, in one method of imprinting a 9 mm$^2$ stamp can be applied to single layer thin films of NPG with a force on the order of 1 kN.

These various methods may result in a variety of desired patterns, such as, for example, straight lines, curved lines, dots, circles, ovals, polygons, irregular shapes, etc. and combinations thereof. As shown in FIG. 1, in some embodiments, the stamp pattern can produce a P-NPG substrate with a two-dimensional square grating pattern (i.e., a two-dimensional mesh of raised NPG squares surrounded by densified NPG or an array of unstamped NPG "pillars" surrounded by densified NPG). In some embodiments a P-NPG SERS-active substrate may be fabricated by stamping a NPG film once with a patterned stamp. In some embodiments, the NPG film may be stamped more than once with one or more than one patterned stamp to provide the P-NPG SERS-active substrate.

In some embodiments, the two-dimensional NPG grating structures may include uncrushed, i.e., un-patterned, NPG surface. In some embodiments, the P-NPG may include periodic arrangements of one or more shapes. In some embodiments, the periodic arrangements of shapes can include, without limitation, a square arrangement, a rectangular arrangement, a hexagonal arrangement, or combinations thereof. In some embodiments, the P-NPG may include an ordered two-dimensional grating pattern, such as, without limitation, a square grating pattern, a chessboard-like grating pattern, a triangular grating pattern, a bowtie grating pattern, a pyramidal grating pattern, or combinations thereof. In some embodiments, the P-NPG may include sharp features i.e., shapes, such as, without limitation, a star shape, a triangle shape, a bowtie shape, a pyramid shape, or combinations thereof.

In some embodiments, the P-NPG SERS substrate may comprise a two-dimensional NPG grating on top of a locally crushed uniform NPG substrate, thus combining the advantages of nanoscaled periodic surface morphology with the internal interacting structure of NPG. The locally crushed uniform NPG substrate may be prepared as described above using an unpatterned stamp. Upon imprinting a uniform area, the NPG film is densified. Densifying reduces the thickness and porosity of the NPG film, typically resulting in smaller pore sizes and more metallic dielectric properties P-NPG SERS Substrate Grating Patterns with Various Pitches and Fill Factors Simple SERS substrates comprising P-NPG may be formed having porous protrusions similar to that shown in FIG. 1 of U.S. application Ser. No. 12/790,905, published as U.S. Publication No. 2011/0059538, the contents of which are hereby incorporated by reference in their entirety. In this embodiment, the substrate comprises protrusions extending therefrom. The protrusions may be created with lithography, etching, imprinting, or stamping.

Some embodiments may include P-NPG substrate with a grating pattern. The grating pattern can have pitches of, without limitation, about 100 nm to about 100 µm, about 200 nm to about 2 µm, about 250 nm to about 850 nm, or about 450 nm to about 650 nm. In some embodiments, the pitches can be from about 250 nm to about 750 nm, about 350 nm to about 650 nm, or about 400 nm to about 600 nm. In some embodiments, the grating pattern can have pitches of, for example, less than about 750 nm, less than about 650 nm, less than about 550 nm, less than about 450 nm, less than about 350 nm, and less than about 250 nm. In some embodiments, the grating pattern can have pitches of, for example, more than about 200 nm, more than about 300 nm, more than about 400 nm, more than about 500 nm, more than about 600 nm, more than about 700 nm, or more than about 800 nm. Pitch refers to the distance between corresponding parts of a repeated pattern. For example, pitch (also referred to as "grating periodicity" and denoted with "Λ", e.g., Λ=650 nm) may refer to the distance between corresponding protrusions in a repeating pattern as set forth in the preceding paragraph. The "optimal" pitch can vary with the wavelength of laser light being used, and thus, different laser systems may have different preferred pitches.

Fill factor (also referred to as "duty cycle" and denoted with "f", e.g., f=80%) refers to the percentage of the pitch of a P-NPG substrate that is not patterned, i.e., imprinted by a stamp. For example, if NPG has been imprinted with a stamp having a grating pattern with a pitch of 500 nm, an 80% fill factor would correspond to 400 nm squares of uncrushed NPG surrounded by 100 nm crushed NPG regions. In some embodiments, the grating pattern may have a fill factor of at least about 50%, at least about 60%, at least about 65%, at least about 70%, at least about 75%, at least about 80%, at least about 85%, at least about 90%, or at least about 95%. In some embodiments, the grating pattern may have a fill factor of less than about 98%, less than about 95%, less than about 90%, less than about 85%, less than about 80%, less than about 75%, less than about 70%, less than about 65%, less than about 60%, or less than about 55%. In some embodiments, the grating pattern may have a fill factor of about 50% to about 98%, about 55% to about 95%, about 60% to about 90%, or about 65% to about 85%.

SERS Signal Intensity Enhancement

The SERS enhancement factor is determined from the following equation:

$$EF=(I_{SERS}/N_{SERS})/(I_{RF}/N_{RF}) \quad (I)$$

where $I_{SERS}$ and $I_{RF}$ are the intensities of a specific Raman line for the SERS substrate and non-enhancing reference sample, respectively. $N_{SERS}$ and $N_{RF}$ are the numbers of probed molecules in the laser spot for the SERS substrate and reference sample, respectively. The intensity can be taken from the peak value or maybe calculated from the integral of the Raman line of the measured spectrum from which the background has been subtracted and normalized by the laser power and CCD integration time. Adapted from Chu et al., *ACS Nano*, 2010, 4, 2804.

When using the P-NPG SERS substrate of the present application, SERS signal intensity enhancement by a factor of at least about $1\times10^5$, at least about $1\times10^6$, at least about $1\times10^7$, at least about $1\times10^8$, at least about $1\times10^9$, at least about $1\times10^{10}$, at least about $1\times10^{11}$, or at least about $1\times10^{12}$ compared to the SERS intensity from a non-enhancing surface can be realized. In some embodiments, the SERS signal enhancement compared to the SERS intensity from a non-enhancing surface may be about $1\times10^5$ to about $1\times10^{12}$, about $1\times10^6$ to about $1\times10^{11}$, or about $1\times10^7$ to about $1\times10^{10}$.

Some embodiments provide a SERS substrate comprising patterned nanoporous gold film where the patterned gold film enhances the SERS signal intensity by a factor of at least about $1\times10^2$, at least about $2\times10^2$, at least about $3\times10^2$, at least about $4\times10^2$, at least about $5\times10^2$, at least about $6\times10^2$, at least about $7\times10^2$, at least about $8\times10^2$, at least about $9\times10^2$, at least about $1\times10^3$, at least about $2\times10^3$, at least about $3\times10^3$, at least about $4\times10^3$, at least about $5\times10^3$, at least about $6\times10^3$, at least about $7\times10^3$, or at least about $8\times10^3$ compared to the same nanoporous gold film without patterning. Some embodiments provide a SERS substrate comprising patterned nanoporous gold film where the patterned gold film enhances the SERS signal intensity by a factor of about $1\times10^2$ to about $8\times10^3$, about $2\times10^2$ to about $7\times10^3$, about $3\times10^2$ to about $6\times10^3$, or about $4\times10^2$ to about $5\times10^3$ compared to the same nanoporous gold film without patterning.

Analyte Detection

A P-NPG SERS substrate of the present application can be used for both qualitative and quantitative analysis of chemical and biological molecules using, e.g., SERS. A P-NPG SERS substrate made using the methods of the present application may be useful for detecting analytes from any source, including, but not limited to air samples, gas samples, bodily fluids, food samples, water samples, homogenized tissue from organisms, etc. Biological samples may include, but need not be limited to, urine, blood, plasma, serum, saliva, semen, stool, sputum, cerebral spinal fluid, tears, exhaled breath, or mucus.

The P-NPG SERS substrate may be used to detect the presence of a particular analyte, for example, a nucleic acid, oligonucleotide, protein, enzyme, antibody, or antigen. The P-NPG SERS substrate may be used to screen bioactive agents, e.g. drug candidates, for binding to a particular analyte in a biological sample or to detect the presence of agents, such as pollutants, in a biological sample. Analytes for which a probe moiety, such as a peptide, protein, oligonucleotide or aptamer, may be designed can be detected using the disclosed P-NPG SERS substrate. The P-NPG SERS substrate may also be used to screen, without limitation, chemicals with a known Raman signature and explosives (e.g., trinitrotoluene ("TNT"), 2,4-dinitrotoluene ("DNT"), hexamethylene triperoxide diamine ("HMDT") etc.).

Analytes include chemical and biological species that may be detected by the polynucleotide analytes such as those polynucleotides defined below. These species may include, but are note limited to, chemical agents, small molecules, pharmaceutical compounds, amino acids, hormones, proteins, lipids, genetic material, cells, viruses, bacteria, and other microorganisms. Genetic material may include, but need not be limited to, m-RNA, r-RNA, t-RNA, DNA, DNA-RNA duplexes, etc. Analytes may also includes receptors that are polynucleotide binding agents, such as, for example, restriction enzymes, activators, repressors, nucleases, polymerases, histones, repair enzymes, chemotherapeutic agents, and the like, that can be detected using the P-NPG SERS substrate.

Additionally, the porous materials may be functionalized with selective binding species to achieve greater specificity. Selective binding species may include, but are not limited to, proteins (including without limitation enzymes, antibodies or fragments thereof), glycoproteins, peptidoglycans, carbohydrates, lipoproteins, a lipoteichoic acid, lipid A, phosphates, nucleic acids that are expressed by certain pathogens (e.g., bacteria, viruses, multicellular fungi, yeasts, protozoans, multicellular parasites, etc.), or organic compounds such as naturally occurring toxins or organic warfare agents, etc. In particular, any number of antibodies may be used to functionalize a sensor to give the sensor specific sensitivity to antigens against which the antibodies are raised. The selective binding species may also be an oligomer of nucleic acids, allowing the sensor to be used for genetic screening. For example, any nucleotides comprising a polynucleotide, such as adenine, cytosine, guanine or thymine linked to 2'-deoxyribose, or ribonucleotides such as adenine, cytosine, guanine or uracil linked to ribose may be used. A polynucleotide or oligonucleotide may also contain nucleotide analogs, including non-naturally occurring synthetic nucleotides or modified naturally occurring nucleotides. Such nucleotide analogs are well known in the art and commercially available, as are polynucleotides containing such nucleotide analogs.

All references identified herein are hereby incorporated by reference in their entireties unless otherwise stated. In the event of any inconsistencies between the present application and these references, the present application shall control.

EXAMPLES

Example 1

Fabrication of Patterned Nanoporous Gold ("P-NPG") SERS Substrates

Preparation of Supported Nanoporous Gold Leaf ("NPGL")

Methods of fabricating nanoporous gold leaf ("NPGL") are known in the art. See, e.g., Ciesielski et al., "Functionalized Nanoporous Gold Leaf Electrode Films for the Immobilization of Photosystem I," ACS Nano. 2008, 2, 2465-2472. Briefly, a gold alloy (Monarch 12K, 49% Au, 51% Ag) with the thickness of approximately 100 nm was dealloyed in 70% $HNO_3$ (Fisher Scientific) for about 15 minutes at about 22° C. to dissolve the silver. The dealloyed NPGL was transferred from the $HNO_3$ solution to deionized water ("DI-water") using a glass slide. The free-floating NPGL was transferred to a silicon (100) wafer (Montco Silicon) that was premodified with 150 nm of gold (J&M Precious Metals) by thermal evaporation and with 1,6-hexanedithiol (Sigma-Aldrich) (1 mM in ethanol for 1 hour) to chemically bind the NPGL and form supported NPGL.

By adjusting the dealloying time, the pore size can be controlled to be in the range of about 5 nm to about 100 nm. SEM imaging of the supported NPGL revealed pore openings of approximately 15 nm after the 15 minute dealloying at room temperature.

Silicon Stamp Preparation

Silicon stamps (9 $mm^2$) were prepared from boron doped p+ type Si(100) wafers with a resistivity of 0.01-0.02 Ωcm and a thickness of 475-550 µm (University Wafer) using standard contact lithography and reactive-ion etching techniques in a similar manner as previously reported. See, Ryckman et al. "Porous Silicon Structure for Low-cost Diffraction-based Biosensing," Appl. Phys. Lett. 2010, 96, 171103. The fabricated silicon stamps consisted of two-dimensional gratings with an etching depth of approximately 300 nm.

Preparation of Patterned Nanoporous Gold ("P-NPG") SERS Substrate

Imprinting of NPG was performed with a Tinius Olsen Super L 60K universal testing machine configured to apply a flat metallic plate onto the backside of the stamp, which was fixed face down on the nanoporous gold with single-sided Scotch Tape. After bringing the plate into contact with the backside of the stamp, a computer-controlled force (about 100 lb to about 650 lb or about $4.5 \times 10^2$ N to about $2.7 \times 10^3$ N) was delivered and sustained for less than about 1 second in order to fully transfer the two-dimensional grating pattern onto the NPGL.

Simultaneously a locally crushed NPG substrate beneath the transferred grating pattern was formed due to the applied force.

Determination of the Detection Sensitivity of the P-NPG Substrate

The detection sensitivity of the P-NPG substrate was investigated through detecting a monolayer of benzenethiol molecules.

The P-NPG substrate was immersed in a 0.2 mM benzenethiol (Acros Organics) solution in ethanol (Fisher Scientific) for one hour, and the samples were subsequently rinsed with ethanol and dried with nitrogen. SERS spectra were collected with an XpioRA 730 Raman microscope (Horiba Jobin Yvon) under 100× magnification with integration time of 20 s and five accumulations. The Raman microscope was run under low power of 9 mW from a 785 nm diode laser with a spot size on the order of 1 µm. Normal incidence of light was used in all SERS measurements, although light was focused over a wide angular range (2θ≈128°) due to the large numerical aperture of the 100× microscope objective lens (NA=0.90), which enabled the stable and reproducible SERS signals in practical SERS measurements.

Results

Figure 2:
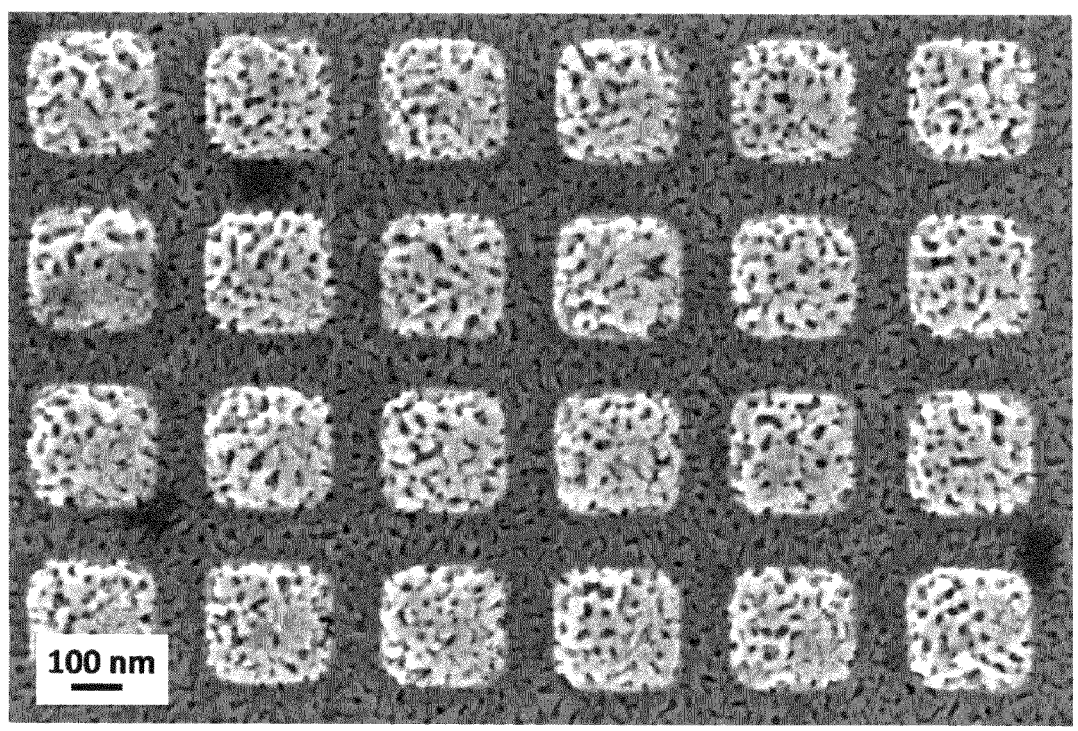
FIG. 2 shows a top-view SEM image of a two-dimensional P-NPG SERS substrate.

FIG. 2 shows the plan-view SEM image of a representative surface morphology of a P-NPG structure prepared at $1.5 \times 10^3$ N with grating period Λ=350 nm and duty cycle f=70%. The SEM image clearly revealed that the pore opening on the grating ridges (un-stamped region) was still retained, while the pore opening on the grating grooves (stamped region) were significantly reduced due to the crush effect, which leads to a densified interacting nanoscaled structure of NPG.

Figure 3:
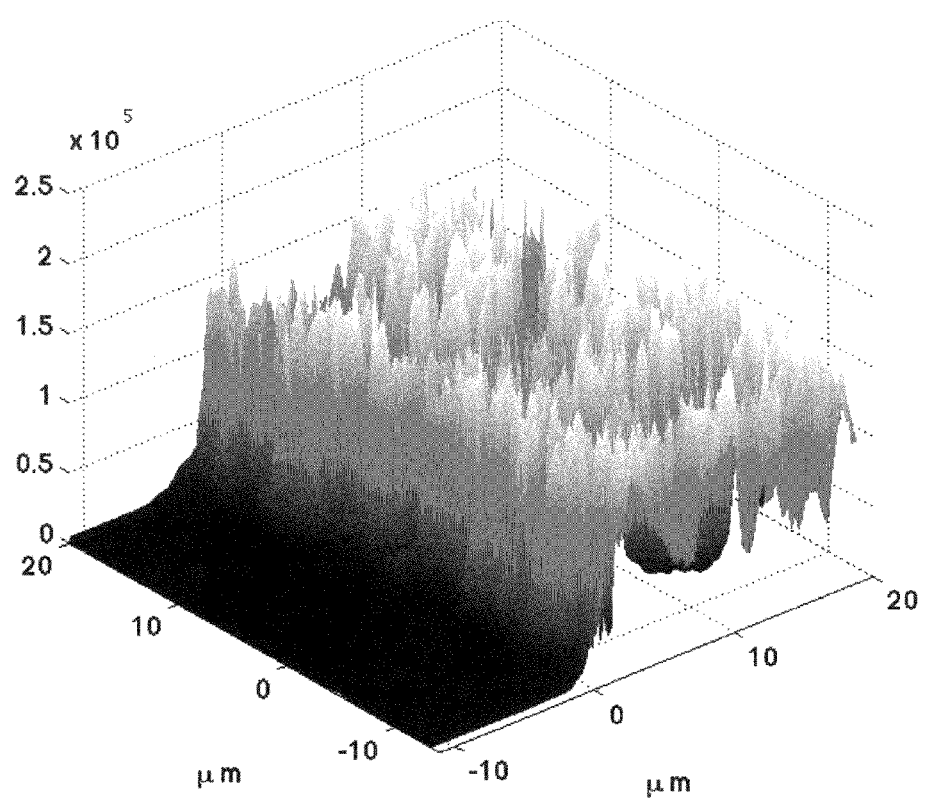
FIG. 3 shows three-dimensional mapping of the SERS intensity measured at the interface of unstamped nanoporous gold ("NPG") and stamped P-NPG.

Since the spot size of laser beam is approximately 1 µm, which is larger than both small pores of NPG and even the artificially created grating squares, reproducible and uniform spectra intensity can be expected across the stamping area. FIG. 3 shows the three-dimensional mapping at the interface between the stamped P-NPG region and the uncrushed NPG region. It is clear that the field enhancement in both regions is relatively uniform, and a significantly enhanced SERS signal can be observed in the stamped P-NPG region.

Another two-dimensional gratings associated P-NPG SERS substrate was prepared with 650 lb force on a 9 $mm^2$ stamp and tested under the experimental conditions described above. An AFM image (not shown) revealed an approximately 60 nm deep grating ridge under the 650 lb pressure. The 60 nm deep grating structures enable the enhanced SERS signal to be emitted into a large angular range for easier collection and measurement with the Raman microscope.

Figure 4:
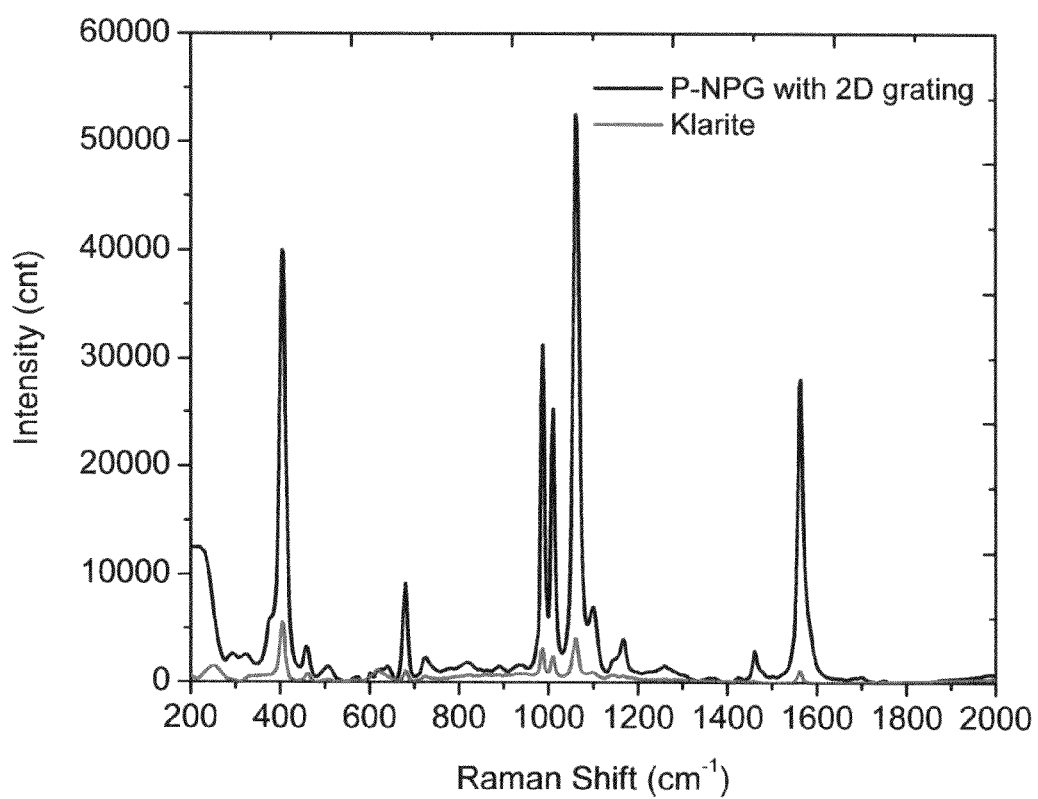
FIG. 4 shows SERS spectra of benzenethiol molecules adsorbed on a commercially-available SERS substrate and a substrate of the present application.

FIG. 4 shows the SERS signal spectrum of a 650 nm pitch P-NPG substrate (upper peaks) and in order to emphasize the efficient SERS signal from this new substrate, the same benzenethiol molecule was absorbed on the KLARITE™ commercial SERS substrate (lower peaks) as a comparison. The KLARITE™ SERS substrate consisted of gold-coated textured silicon (regular arrays of 1 µm wide and 500 nm deep holes) mounted on a glass microscope slide. Compared to a non-enhancing surface, the enhancement factor of KLARITE™ substrate for binding molecules has been reported to be $>10^6$. Therefore it can be concluded that the two-dimensional grating associated P-NPG substrate can achieve at least a $10^7$ SERS enhancement, at least one order of magnitude higher than that of KLARITE™ commercial substrate, by comparing the peak height at 1071 $cm^{-1}$ band.

Figure 5:
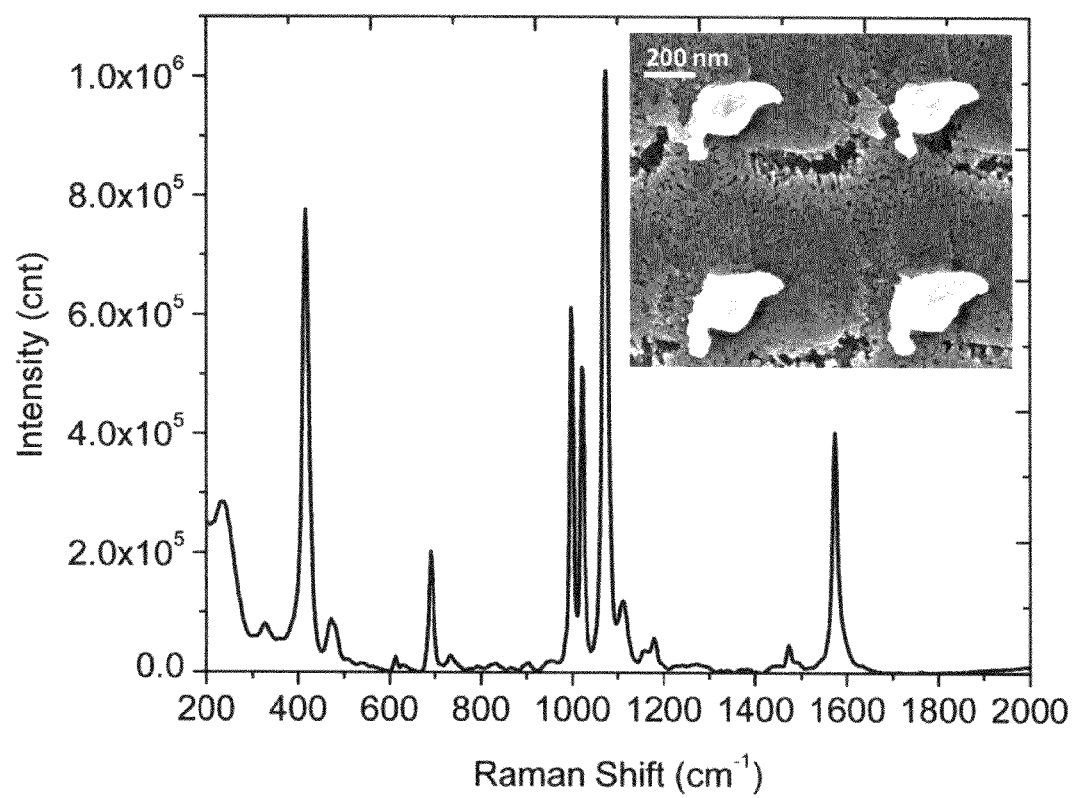
FIG. 5 shows SERS spectrum of benzenethiol molecules absorbed on a P-NPG SERS substrate with modified shape, which is shown in the SEM image in the inset.

A SERS enhancement of about $2 \times 10^8$ was measured from a large 10×10 µm region of triangular periodic gratings associated with the crescent-shaped fracture of NPG due to high shear force, as shown in FIG. 5, that was formed in one region of the sample due to a sheer force applied during the stamping process. Though not wishing to be bound by a particular theory, based on the SEM image, the drastic enhancement may be attributed to sharp tips located at both triangular grating edges and the crescent fractal NPG, which leads to much stronger field at those tips. Based on this observation, fabrication of grating structures with sharp features, such as a star, bowtie, or pyramid-shaped gratings is likely to further increase the SERS enhancement.

In order to isolate the influences of the grating structure and the crushed NPG film on the enhanced SERS signal, the crushed NPG film generated by pressing a 9 mm² silicon square (unpatterned) into it was investigated.

Figure 6:
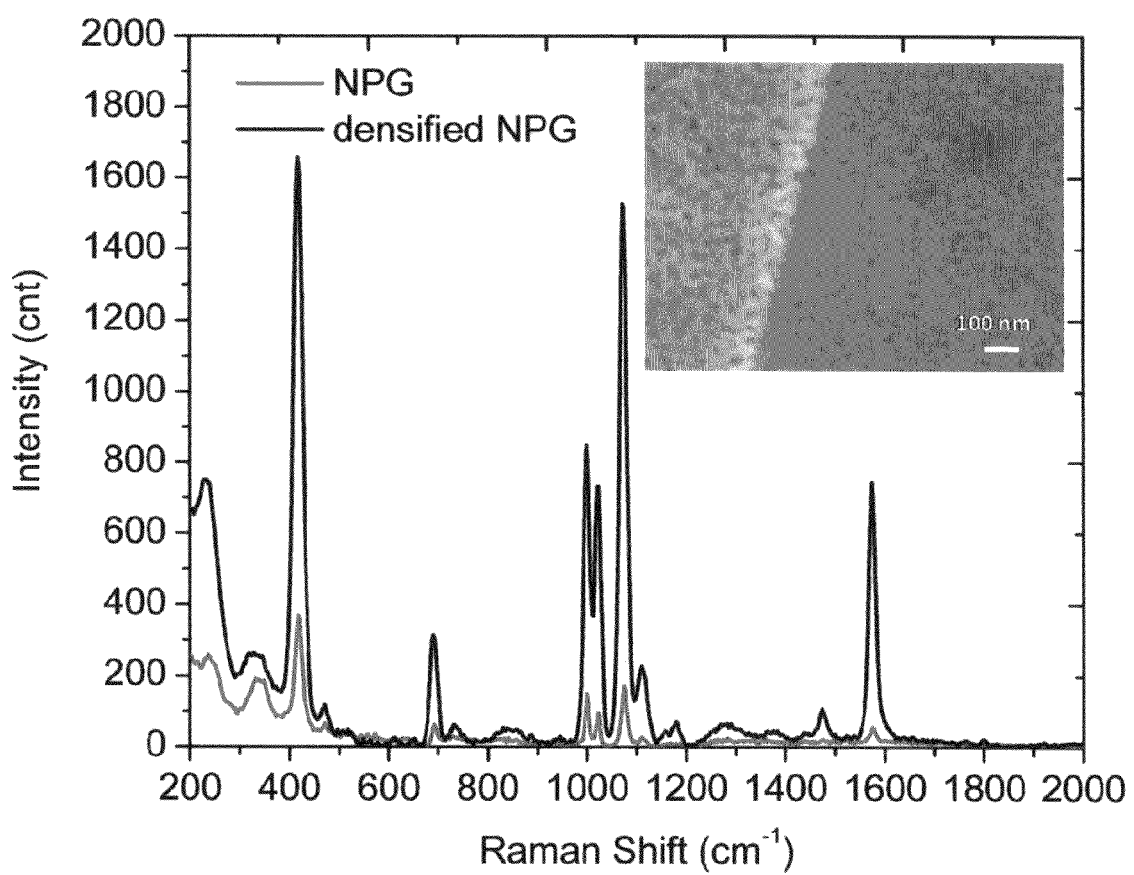
FIG. 6 shows SERS spectra of benzenethiol molecules absorbed on NPG film, and densified NPG, and an SEM image of the interface of densified (right) and as-prepared NPG (left) (inset).

FIG. 6 shows the SERS spectra of benzenethiol absorbed on uncrushed NPG (lower peaks) and NPG crushed by a large area, unpatterned silicon stamp (upper peaks). Inset shows the SEM image of the interface between crushed and uncrushed NPG film. It is clear that the surface topology and corresponding SERS response has been significantly changed by the pressure, and crushed unpatterned NPG shows 10 to 15 times higher SERS signal than that of the uncrushed NPG substrate.

Previous work (Qian et al., "Surface Enhanced Raman Scattering of Nanoporous Gold: Smaller Pore Sizes Stronger Enhancements," *Appl. Phys. Lett.* 2007, 90, 153120) has shown that NPG samples with smaller pores can generate stronger enhancement, and modified NPG via electroless plating showed even higher SERS signal due to the Combination of small pore size and large gold ligament. Under the applied pressure, the pore size or the distance between the neighboring gold ligaments may be decreased and a strong localized field can be generated at those pores where the molecules were attached, which may significantly enhance the SERS signal. Similar work can be found in previous study (Lang et al., "Geometric Effect on Surface Enhanced Raman Scattering of Nanoporous Gold: Improving Scattering by Tailoring Ligament and Nanopores Ratios," *Appl. Phys. Lett.* 2009, 94, 213109) and it also proved the conclusion in previous studies that the higher SERS enhancement could be achieved by the smaller pores. By comparing the peak heights of spectra in FIGS. 3, 4, and 5, it can be concluded that the stamped gratings on top provides the dominant contribution to the SERS enhancement, since the crushed P-NPG film with two-dimensional NPG gratings showed at least two orders larger magnitude of spectrum peak height than that of uncrushed NPG.

Figure 7:
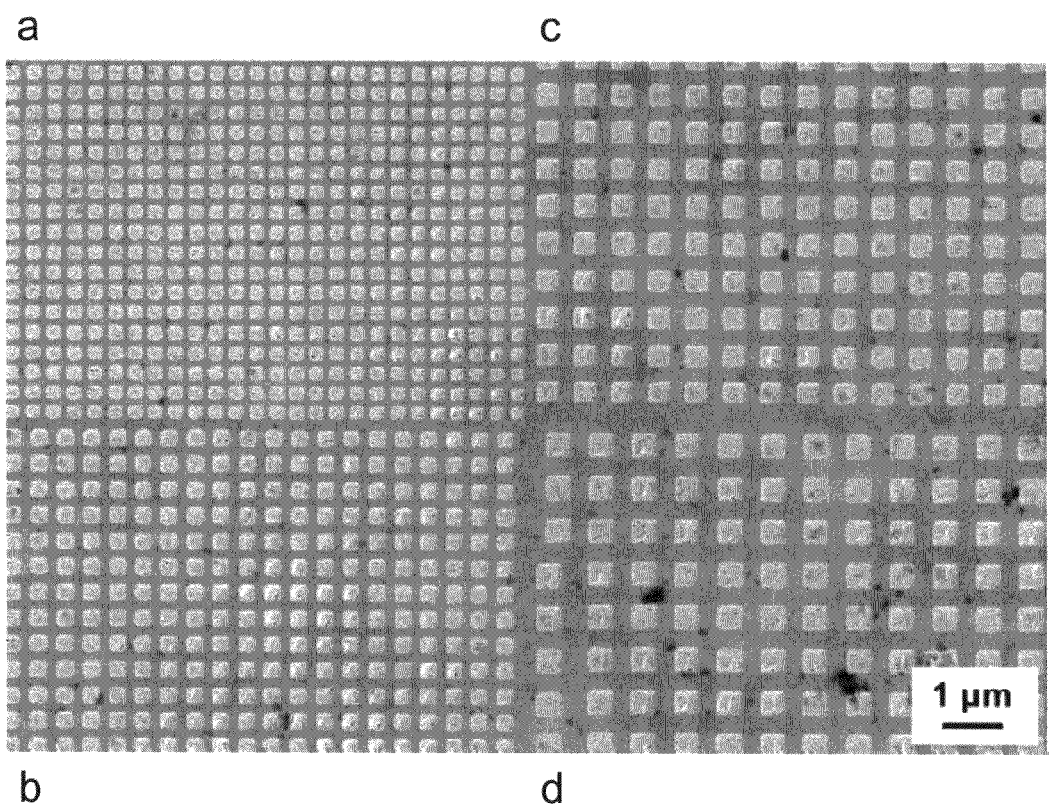
FIG. 7 shows SEM images of stamped two-dimensional P-NPG SERS substrates with air fill factors of approximately 40% (±10%) and pitches of (a) 350 nm, (b) 450 nm, (c) 650 nm, and (d) 750 nm.

In order to further investigate the contribution of the grating pattern to the optimized SERS enhancements of our stamped P-NPG samples, a SERS substrate consisting of four grating patterns was fabricated, as shown in FIG. 7. Referring to FIG. 7, each pattern contained a two-dimensional grating structure with pitches of (a) 350 nm, (b) 450 nm, (c) 650 nm, and (d) 750 nm. The SEM image revealed the air fill fraction of approximately 40% (±10%) along both x and y directions. As is known, a strong SERS signal is closely related to the surface plasmon excitation for the grating-based SERS substrates; however, the corresponding incident angle is required to be accurately adjusted for the specific grating structure, especially for the shallow grating (i.e., about 2 nm to about 40 nm). To avoid the critical angle adjustment for shallow gratings, a deep grating (i.e., about 60 nm to about 100 nm) was used for a broader resonance angular range.

Figure 8:
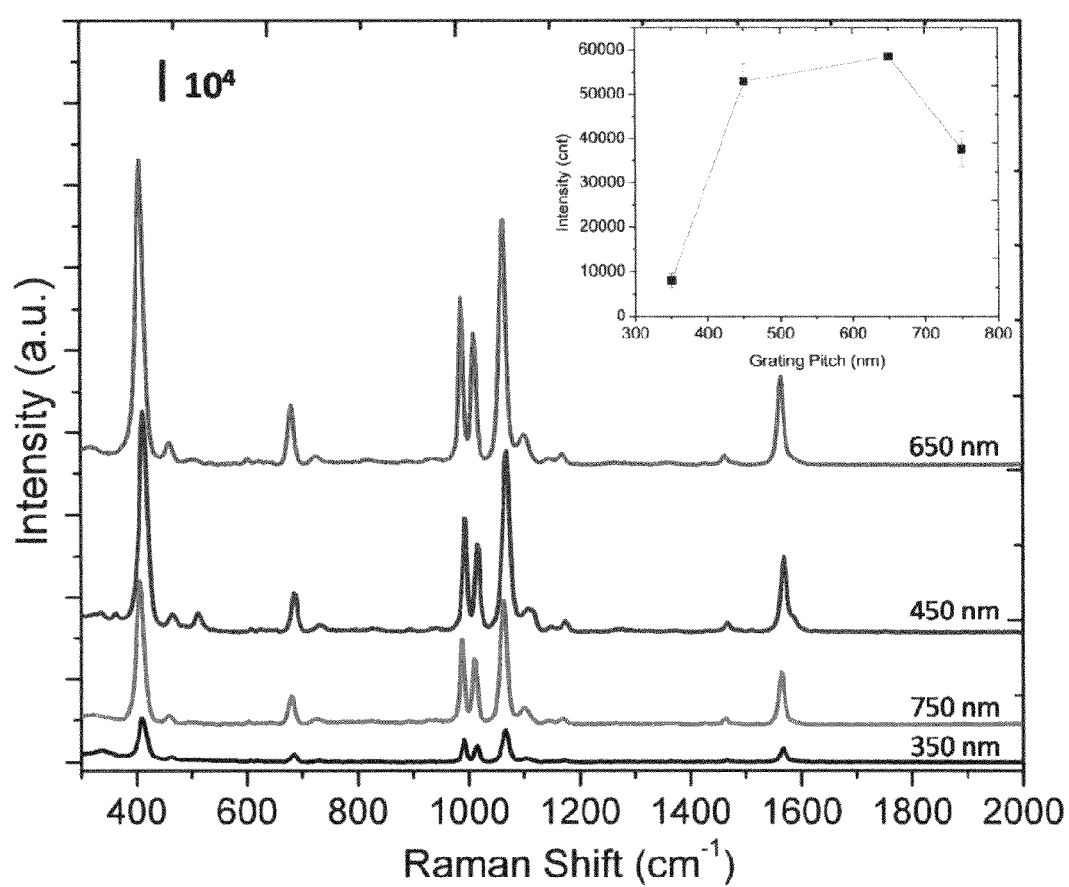
FIG. 8 shows SERS spectra of benzenethiol absorbed on P-NPG substrates with different grating pitches. Inset shows intensities at the 1070 $cm^{-1}$ band.

FIG. 8 shows the influence of the grating pitch on the SERS enhancement factor at normal incidence by comparing the peak intensity of 1070 $cm^{-1}$ band at 783.8 nm incident wavelength. High SERS intensity was observed for all grating pitches, although the highest SERS signal (approximate increase in signal intensity of one order of magnitude) was from a substrate with a grating pitch between 450 nm and 650 nm. Though not wishing to be bound by a particular theory, the grating-pitch related SERS signal enhancement may be a result of the efficiency of activation of plasmon resonance. Reduction of the SERS signal from the 350 nm pitch sample can thus be attributed to its being out of the plasmon resonance range or less efficient plasmon coupling.

Summary

A simple stamping technique was used to demonstrate a fast fabrication of NPG based SERS-active substrate. Such SERS template consisting of nanoscaled surface topology created by one-step stamping showed efficient and reproducible SERS enhancement. The well-organized two-dimensional periodic NPG gratings and a crushed NPG film beneath were shown to both contribute to the significantly enhanced SERS intensity. After the optimization of the grating pitch, at least one order higher magnitude of SERS spectrum was observed based on a 650 nm pitch with 60 nm deep grating structure than that of the KLARITE™ commercial substrate. SERS enhancement factor greater than $10^9$ could be achieved from gratings with much sharper features.

Example 2

Preparation of Supported NPGL

The NPG is prepared from a gold alloy (49% Au, 51% Ag) with the thickness of approximately 100 nm, and dealloyed in 50%, 60%, 70%, 80%, or 90% $HNO_3$ or HCl for about 2 hours or less, about 1 and half hours or less, about 1 hour or less, about 45 minutes or less, about 30 minutes or less, about 25 minutes or less, about 20 minutes or less, about 15 minutes or less, about 12.5 minutes or less, about 10 minutes or less, about 7.5 minutes or less, about 5 minutes or less, about 2.5 minutes or less, about 2 minutes or less, about 1.5 minutes or less, about 1.0 minutes or less, or about 0.5 minutes or less at about 22° C. to fully or partially dissolve the silver. By adjusting the dealloying time, temperature, concentration of the acid, or a combination thereof, the percentage of the dissolved element can be controlled. The NPGL can therefore be dealloyed wherein the percentage of the dissolved element may be about 10% or more, about 15% or more, about 20% or more, about 25% or more, about 30% or more, about 35% or more, about 40% or more, about 45% or more, about 50% or more, about 55% or more, about 60% or more, about 65% or more, about 70% or more, about 75% or more, about 80% or more, about 85% or more, about 90% or more, about 95% or more, or about 100% of the element content of the alloy. The dealloyed NPGL is then transferred from the $HNO_3$ or HCl solution to DI-water using a glass slide. The free-floating NPGL is transferred to a silicon (100) wafer that is premodified with 150 nm of gold by thermal evaporation and with 1,6-hexanedithiol (1 mM in ethanol for 1 hour) to chemically bind the NPGL and form supported NPGL.

What is claimed is:

1. A SERS substrate comprising patterned nanoporous gold film having a plurality of raised features, the patterned nanoporous gold film being supported on a substrate surface which directly underlies the gold film, wherein each of the plurality of raised features of the patterned nanoporous gold film has a topography which is unrelated to the topography of the directly underlying substrate surface, wherein the patterned gold film enhances the SERS signal intensity by a factor of at least about $4\times10^2$ compared to the same nanoporous gold film without patterning.

2. The SERS substrate of claim 1, wherein the gold film of the raised features has a porosity of greater than about 10%, wherein the raised features are surrounded by portions of the gold film having lower porosity than the raised features, wherein the porosity of the nanoporous gold film comprises a ratio of a volume of empty space within the film over a volume of the film, and wherein the nanoporous gold film comprises pores that are smaller than about 500 nm.

3. The SERS substrate of claim 2, wherein the raised features have a width of less than about 100 μm.

4. The SERS substrate of claim 2, wherein the raised features have a height of less than about 1 μm.

5. The SERS substrate of claim 2, wherein the raised features have a porosity greater than about 50%.

6. The SERS substrate of claim 2, wherein the raised features have a porosity greater than about 70%.

7. The SERS substrate of claim 2, wherein the raised features have a width of less than about 10 μm.

8. The SERS substrate of claim 2, wherein the raised features have a height of less than about 200 nm.

9. The SERS substrate of claim 1, wherein the patterned nanoporous gold film comprises a grating pattern with a pitch of about 350 nm to about 850 nm.

10. The SERS substrate of claim 1, wherein the patterned nanoporous gold film has a fill factor of about 50% to about 90%.

11. The SERS substrate of claim 1, wherein the patterned nanoporous gold film includes a square grating, a star-shaped grating, a bowtie-shaped grating, a pyramid-shaped grating, or combinations thereof.

12. The SERS substrate of claim 1, wherein the patterned nanoporous gold film comprises pores that have a diameter of about 5 nm to about 50 nm.

13. The SERS substrate of claim 1, wherein the patterned nanoporous gold film has a porosity of about 40% to about 60%.

14. The SERS substrate of claim 1, wherein the patterned nanoporous gold film has a thickness of about 50 nm to about 100 μm.

15. A method of preparing a SERS substrate, the method comprising:
   providing a substantially flat first nanoporous gold film, the gold film being supported on a substrate surface which directly underlies the gold film; and
   imprinting the first nanoporous gold film with a stamp having a regularly-repeating pattern, comprising applying pressure to the nanoporous gold film to transfer the regularly-repeating pattern to the nanoporous gold film; and
   removing the stamp to reveal the patterned nanoporous gold film, wherein the patterned nanoporous gold film has a topography which is unrelated to the topography of the directly underlying substrate surface.

16. A method of detecting an analyte, the method comprising:
   contacting a SERS substrate with a sample suspected of containing an analyte of interest; and
   obtaining a SERS spectrum of the sample,
   wherein the SERS substrate comprises a nanoporous gold film having a pattern defined therein, the pattern comprising a plurality of raised features, the nanoporous gold film being supported on a substrate surface which directly underlies the gold film, wherein each of the plurality of raised features defined in the nanoporous gold film has a topography which is unrelated to the topography of the directly underlying substrate surface.

* * * * *